Figure 1:
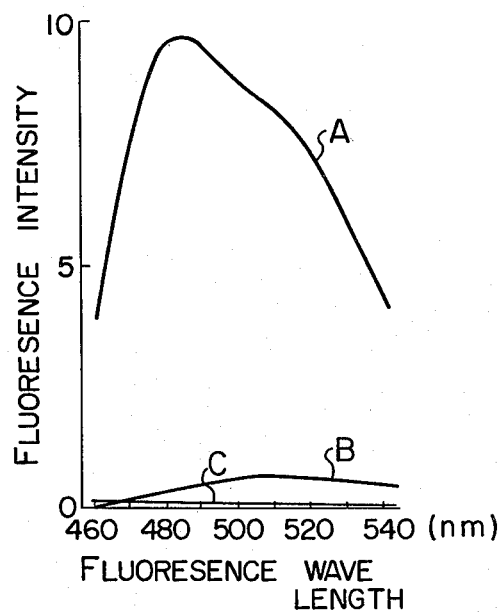

United States Patent [19]

Nakajima et al.

[11] 4,438,206
[45] Mar. 20, 1984

[54] METHOD FOR DETERMINATION OF FORMALDEHYDE

[75] Inventors: Motoo Nakajima; Kiyoshi Mizusawa, both of Noda, Japan

[73] Assignee: Kikkoman Corporation, Noda, Japan

[21] Appl. No.: 441,926

[22] Filed: Nov. 15, 1982

[30] Foreign Application Priority Data

Nov. 19, 1981 [JP] Japan ................................ 56-184492

[51] Int. Cl.³ ...................... G01N 21/64; G01N 21/77
[52] U.S. Cl. ...................................... 436/130; 436/172
[58] Field of Search ......................... 436/128, 130, 172

[56] References Cited

U.S. PATENT DOCUMENTS 4,204,839  5/1980  Wu et al. ........................ 436/172 X

OTHER PUBLICATIONS

Nash, *Biochem. J.* 55: 416-421, (1953).
Sawicki et al., *Anal. Chem.* 34:1460-1464, (1962).
Dickinson et al., *Chem. Comm.* 13:1719-1720, (1970).
Rose et al., Methods in Enzymology IX: Carbohydrate Metabolism, pp. 357-360, (W. Wood, Ed. 1966).
Belman, *Anal. Chim. Acta* 29:120-126, (1963).

*Primary Examiner*—Arnold Turk
*Assistant Examiner*—Robert J. Hill, Jr.
*Attorney, Agent, or Firm*—Schuyler, Banner, Birch, McKie & Beckett

[57] ABSTRACT

In a method of formaldehyde determination by measuring the fluorescence of a fluorescent substance formed by allowing a formaldehyde-containing solution to react with a reagent capable of forming said fluorescent substance from formaldehyde, the improvement comprising measuring the fluorescence in the presence of a serum albumin.

4 Claims, 2 Drawing Figures

METHOD FOR DETERMINATION OF FORMALDEHYDE

This invention relates to a method of formaldehyde determination which allows extremely small amounts of formaldehyde to be determined.

Formaldehyde is used in manufacturing synthetic resins such as phenol resins, urea resins, melamine resins, aniline resins, and casein resins. It is used also in improving the strength of textile fibers or improving the fiber strength in paper making and in hardening of plastic films. Further, it is used as a raw material in the production of ethylene glycol, urotropin, rubber chemicals, dyes, and other chemicals. In addition, it is used as a fungicide or antiseptic.

It has been known that there are some of the daily necessaries such as tablewares, plywood furnitures, and clothing articles which liberate a small amount of formaldehyde either in vapor state or as dissolved in water. The liberated formaldehyde is harmful to the human body, causing sometimes a poisoning which may lead to a rash.

For the above reasons, the determination of formaldehyde is important in the above-noted industrial fields as well as from the standpoint of hygienic chemistry. Moreover, since formaldehyde is produced as a reaction product during the course of several enzymatic reactions, the determination of formaldehyde is important in assaying the enzymatic activities in said reactions or the substrate concentrations before the occurrence of enzymatic reactions.

For the determination of formaldehyde, there have heretofore been known several methods, as described below, which, however, do not sufficiently meet the requirement because of the unsatisfactory detection sensitivity.

(1) A method in which formaldehyde is allowed to react with an acetylacetone reagent in the presence of an ammonium salt and the resulting diacetyldihydrolutidine is determined by colorimetry [T. Nash, Biochem. J., Vol. 55, pp. 416–21 (1953)]. (2) A method in which formaldehyde is allowed to react with sodium chromotropate with heating in an acidic medium containing sulfuric acid and the developed color is colorimetrically measured [E. Sawicki et al., Anal. Chem., Vol. 34, pp. 1460–64 (1962)]. (3) A method in which formaldehyde is allowed to react with 4-amino-3-hydrazino-5-mercapto-1,2,4-triazole in an alkaline medium and, after oxidizing the reaction mixture with periodic acid, the colored solution is colorimetrically analyzed [R. G. Dickinson et al., Chem. Comm., pp. 1719–1720 (1970)]. (4) A method in which the oxidation of formaldehyde is effected by means of formaldehyde dehydrogenase and the resulting NADH is colorimetrically determined [Z. B. Rose et al., Methods in Enzymology, Vol. 9, pp. 357–60 (1966)]. These methods have a disadvantage of being unsuitable for the determination of an extremely small amount of formaldehyde because of an insufficient color development of the color-forming substance. In a modified method the diacetyldihydrolutidine formed by the reaction of formaldehyde with the acetylacetone reagent in the presence of an ammonium salt is fluorimetrically determined [S. Belman, Anal. Chim. Acta, Vol. 29, pp. 120–6 (1963)]. This method is also unsuitable for the determination of an extremely small amount of formaldehyde because of the insufficient detection sensitivity due to the low fluorescence intensity of the formed fluorescent substance.

Under the circumstances, the present inventors made an extensive study to find a method for detecting, with satisfactory sensitivity, an extremely small amount of formaldehyde. As a result it was found that an extremely small amount of formaldehyde becomes detectable with a high sensitivity when the fluorimetric determination is performed in the presence of a serum albumin, especially bovine serum albumin, the addition of which markedly increases the fluorescence intensity of the fluorescent substance, resulting in an increase in formaldehyde detection sensitivity by more than tenfold. Based on this finding, this invention has been accomplished.

An object of this invention is to provide a highly sensitive method for the determination of an extremely small amount of formaldehyde.

Other objects and advantages of this invention will become apparent from the following description.

According to this invention, there is provided an improved method of formaldehyde determination by measuring the fluorescence of a fluorescent substance formed by the reaction of a formaldehyde-containing solution with a reagent capable of forming said fluorescent substance from formaldehyde, wherein the improvement comprises measuring the fluorescence in the presence of a serum albumin.

In the accompanying drawings,

FIG. 1 shows fluorescence spectra of the product of reaction between the acetylacetone reagent and a formaldehyde-containing solution; curve A is the spectrum of the sample obtained by using bovine serum albumin according to this invention, curve B is that of the sample obtained without using the serum albumin according to the conventional procedure, and curve C is that of the bovine serum albumin alone.

Figure 2:
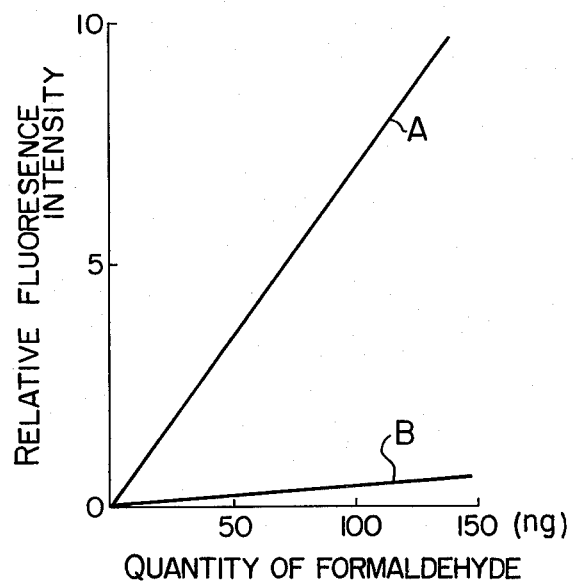

FIG. 2 is a graph (standard calibration curves) representing the relationship between the amount of formaldehyde and the relative fluorescence intensity; straight line A is obtained according to this invention and straight line B according to the conventional procedure.

The method of this invention is described below in detail.

The preparation of the reagent which forms a fluorescent substance by reacting with formaldehyde and the procedure of reacting the reagent with a formaldehyde-containing solution and determining the resulting fluorescent substance are both carried out in the same or essentially the same manner as in the well-known above-mentioned methods of T. Nash and S. Belman. In preparing the reagent, an acetylacetone salt such as lithium or ammonium acetylacetonate or an acetoacetic ester such as methyl or ethyl acetoacetate is dissolved in an ammonium acetate or ammonium phosphate buffer solution to form a solution containing acetylacetone in a molarity of 0.001 to 0.1. The ammonium acetate buffer solution used above is prepared by adjusting an ammonium acetate solution of 0.1 to 3.0, preferably 2, in molarity to pH 4 to 8, preferably 5.5 to 6.5, with an acetic acid or ammonia solution. The ammonium phosphate buffer solution is similarly prepared by adjusting an ammonium phosphate solution of 0.1 to 3.0, preferably 2, in molarity to pH 4 to 8, preferably 5.5 to 7.5, with a phosphoric acid or ammonia solution.

The reaction between the above reagent and formaldehyde is carried out under the conditions such that the reaction mixture is held at a temperature of 20° to 80° C.

for 5 hours to 2 minutes. The holding time is longer at lower temperatures and shorter at elevated temperatures. For instance, the holding time is 5 hours at 20° C., 40 minutes at 37° C., and 5 minutes at 58° C.

The reaction of the reagent and a formaldehyde-containing solution yields in the reaction mixture a fluorescent substance such as diacetyldihydrolutidine. The fluorescence of the reaction mixture is measured at an excitation wave length among 400 to 420, especially 410 to 415, nm and an emission wave length among 470 to 520, especially 480 to 485, nm, respectively.

In the fluorimetric determination of formaldehyde according to this invention, a serum albumin is added to the reaction mixture being analyzed. The type of serum albumin is mot important. Other egg proteins (e.g. chick egg white albumin) and serum proteins (e.g. human γ-globulin, bovine β-globulin, and bovine α-globulin) exhibit no enhancing effect upon the fluorescence intensity of the reaction mixture (see Table 1 of Experimental Example 2 given later).

As the serum albumins for use in the present method, mention may be made of those of human, horse, pig, cattle, goat, dog, rabbit, rat or mouse, ginea pig, chicken, and pigeon. Of these, the bovine serum albumin is most preferred because of its distinguished enhancing effect upon the fluorescence intensity (see Table 1 of Experimental Example 2 given later).

As for the time of addition of a serum albumin, it may be added (1) during the preparation of the reagent capable of forming a fluorescent substance by reacting with formaldehyde, (2) to the formaldehyde-containing solution being analyzed, or (3) during or after the reaction of the formaldehyde-containing solution with the reagent capable of forming a fluorescent substance by reacting with formaldehyde. The amount of serum albumin to be added is 0.1 to 3, preferably 0.6 to 1.8, %(W/V) based on the reaction mixture.

The conventional fluorimetric method for the determination of formaldehyde is reported to be unable to give a sufficiently accurate result unless the formaldehyde concentration is 10 ng/2 ml or more, whereas the present method is able to give a sufficiently accurate result even when the formaldehyde concentration is as small as 2.67 ng/2 ml. It is to be noted that acetylacetone, a salt thereof, or an acetoacetic ester reacts with various aldehydes to form a fluorescent substance in the reaction mixture, the reaction being not characteristic of formaldehyde alone. For instance, acetylacetone reacts with acetaldehyde and exhibits fluorescence excitation and emission at wave lengths of 365 nm and 465 nm, respectively. The addition of a serum albumin in this case, however, does not result in any noticeable increase in the intensity of fluorescence. From this fact, it is evident that the enhancement of fluorescence intensity by the addition of a serum albumin is observable only in the reaction involving formaldehyde.

Further, in the field of clinical chemistry it is a general practice to determine a specific substrate such as uric acid by decomposing with an oxidizing enzyme such as uricase, converting the resulting hydrogen peroxide into formaldehyde in the pesence of an alcohol and catalase, and determining the formaldehyde. The present method is adaptable to the determination of formaldehyde in this case. Accordingly, the present invention makes it possible to perform microanalytical determination of the above specific substrate.

The invention is illustrated below with reference to Experimental Examples and Examples, but the invention is not limited thereto.

EXPERIMENTAL EXAMPLE 1

A standard calibration curve was prepared from the data on interrelation between the quantity of formaldehyde and the relative fluorescence intensity.

I. Preparation of reagents (1) Acetylacetone reagent

A 2 M ammonium acetate buffer solution (adjusted to pH 6.0 with acetic acid) was mixed with 2 ml of acetylacetone, stirred to form a uniform solution, and made up with the same buffer solution to 1 liter.

(2) Standard formaldehyde solution

Formaldehyde was dissolved in distilled water to form solutions containing respectively 2.67, 5.34, 10.67, 16.01, 21.34, 26.68, 53.36, 80.04, 106.7, and 133.4 nanograms (ng) of formaldehyde in 2 ml.

(3) Bovine serum albumin solution

A 6% (W/V) aqueous solution of bovine serum albumin (manufactured by Sigma Co.) was prepared.

II. Determination of formaldehyde

Each 2 ml of the above formaldehyde solutions of different concentrations was mixed with 2 ml of the above acetylacetone reagent. After thorough stirring, the mixture was allowed to react at 37° C. for 40 minutes. The reaction mixture was admixed with 0.5 ml of the bovine serum albumin solution and the formaldehyde content was fluorimetrically determined at fluorescence excitation and emission wave lengths of 415 and 480 nm, respectively. For comparison, the above reaction mixture was admixed with 0.5 ml of water in place of 0.5 ml of the bovine serum albumin solution, and the fluorimetric determination was performed at fluorescence excitation and emission wave lengths of 415 and 510 nm, respectively.

The fluorescence spectrum of the reaction mixture derived from a solution containing 133.4 ng/2 ml of formaldehyde was measured at an excitation wave length of 415 nm and the results obtained were as shown in FIG. 1. The upper curve A represents the fluorescence spectrum of reaction mixture containing the bovine serum albumin and the lower curve B represents that of reaction mixture containing no bovine serum albumin. The curve C represents the fluorescence spectrum of the bovine serum albumin alone, indicating very low intensities in this wave length region.

The fluorimetric determination was performed in all cases under the following conditions:
Spectrofluorimeter: Type FP550 of Nihon Bunko K.K.
Excitation wave length: 415 nm; slit, 10 nm.
Emission wave length: 480 nm [510 nm in the case where no serum albumin is added (conventional method)]; slit, 20 nm.

The blank value was obtained in the same manner as described above, except that 2 ml of distilled water was used in place of 2 ml of the formaldehyde solution.

The relationship between the quantity of formaldehyde and the relative fluorescence intensity (obtained by subtracting the blank value) at 480 nm (510 nm in the case where no serum albumin is added) was as shown in FIG. 2.

It is seen from FIG. 1 that the relative fluorescence intensity maximum of the reaction mixture containing bovine serum albumin according to this invention is as high as about 10 times that of the reaction mixture containing no serum albumin (conventional method).

FIG. 2 shows that there is a linear relation between the quantity of formaldehyde and the relative fluorescence intensity in both cases of the present method and the conventional method. In the conventional method, however, the fluorescence intensity per unit quantity of formaldehyde was very low, suggesting that there is a possibility of incorrect determination when the formaldehyde content is 26.7 ng or below. As contrasted, the sample according to this invention showed a markedly higher relative fluorescence intensity and, as a consequence, an accurate determination is possible on the sample containing as low as 2.67 ng of formaldehyde (about one-tenth the concentration in the conventional method).

EXPERIMENTAL EXAMPLE 2

The fluorimetric determination was carried out in the same manner as in Experimental Example 1, except that 0.5 ml of each additive solution (shown in Table 1 below) was used in place of 0.5 ml of the bovine serum albumin solution (shown in "II. Determination of formaldehyde" in Experimental Example 1). The results obtained were as shown in Table 1. It is seen from Table 1 that the bovine serum albumin is especially suitable.

TABLE 1

| Additive | Relative fluorescence intensity |
| --- | --- |
| None (control) | 1 |
| Bovine serum albumin | 15.2 |
| Human serum albumin | 3.3 |
| Ginea pig serum albumin | 5.5 |
| Mouse serum albumin | 4.1 |
| Egg white albumin | 1 |
| Human γ-globulin | 1 |
| Bovine β-globulin | 1 |
| Bovine α-globulin | 1 |

EXAMPLE 1

To 2 ml of a sample solution containing an extremely small amount of formaldehyde, was added 2 ml of the acetylacetone reagent prepared in Experimental Example 1. After thorough stirring, the solution was allowed to undergo fluorescent substance forming reaction at 37° C. for 40 minutes. To the reaction mixture was added 0.5 ml of the bovine serum albumin solution prepared in Experimental Example 1. The reaction mixture thus treated was subjected to the fluorimetric determination at fluorescence excitation and emission wave lengths of 415 and 480 nm, respectively.

The blank value was obtained in the same manner as described above, except that 2 ml of distilled water was added in place of 2 ml of the formaldehyde-containing sample solution. After subtraction of the blank value, the relative fluorescence intensity was 1.28. From this value, the formaldehyde content was estimated by means of the calibration curve shown in FIG. 2. The formaldehyde content was found to be 18.2 ng in 2 ml of the sample.

EXAMPLE 2

Into distilled water, were dissolved 0.2 ml of acetylacetone, 0.7 g of bovine serum albumin (manufactured by Sigma Co.) together with 10 g of diammonium hydrogen phosphate, 0.3 ml of 85-% phosphoric acid, 10 ml of methanol, 10 mg of catalse (Sigma Co.), and 2 mg of uricase (Boehringer Mannheim Co.). The resulting solution was made up to 100 ml with distilled water and filtered to obtain a fluorescent substance-forming reagent. To 2 μl of a serum, was added 4 ml of the above-mentioned fluorescent substance-forming reagent. The mixture was allowed to react at 37° C. for 60 minutes and left standing for 15 minutes at room temperature. The fluorimetric determination was performed at fluorescence exitation and emission wave lengths of 410 and 480 nm, respectively.

Another fluorimetric determination was carried out in the same manner as described above, except that 2 μl of a standard uric acid solution (5 mg/100 ml, manufactured by Sigma Co.) was used in place of 2 μl of the serum. The blank values of the serum and standard uric acid solution were obtained by fluorimetry in the same manner as above, except that 4 ml of a fluorescent substance-forming reagent containing no uricase was used in place of 4 ml of the above fluorescent substance-forming reagent.

The uric acid content (in mg) of 100 ml of the serum was calculated by dividing the value of relative fluorescence intensity of the serum (after subtraction of the blank value) by the value of relative fluorescence intensity of the standard uric acid solution (after subtraction of the blank value) and multiplying the quotient by 5. The uric acid content of the above serum was found to be 4.1 mg/100 ml. From the above result, it is seen that a specific substance content can be determined with satisfactory accuracy using a very small amount of the serum sample.

What is claimed is:

1. In a method of formaldehyde determination by measuring the fluorescence of a fluorescent substance formed by allowing a formaldehyde-containing solution to react with an acetylacetone reagent capable of forming said fluorescent substance from formaldehyde, the improvement comprising measuring the fluorescence in the presence of a serum albumin.

2. A method according to claim 1, wherein the amount of the serum albumin is 0.6–1.8%(W/V) of the reaction mixture.

3. A method according to claim 1 or 2, wherein the serum albumin is a bovine serum albumin.

4. A method according to claim 1, wherein the acetylacetone reagent is an ammonium acetate or ammonium phosphate buffer solution of 0.1 to 3.0 in molarity containing 0.001 to 0.1 molarity of acetylacetone, lithium acetylacetonate, ammonium acetylacetonate, methyl acetoacetate, or ethyl acetoacetate.

* * * * *